US005166588A

United States Patent [19]
Goldhorn

[11] Patent Number: 5,166,588
[45] Date of Patent: Nov. 24, 1992

[54] MEDICAL APPARATUS HAVING AN APPARATUS PART WHICH IS MOTOR-ADJUSTABLE RELATIVE TO A SURFACE IN A DIRECTION OF AT LEAST ONE DEGREE OF FREEDOM

[75] Inventor: Klaus Goldhorn, Erlangen, Fed. Rep. of Germany

[73] Assignee: Siemens Aktiengesellschaft, Munich, Fed. Rep. of Germany

[21] Appl. No.: 600,423

[22] Filed: Feb. 25, 1991

[30] Foreign Application Priority Data

Mar. 7, 1990 [EP]  European Pat. Off. ........ 90104373.7

[51] Int. Cl.⁵ .............................. A61B 6/10; F16P 3/12
[52] U.S. Cl. .................................... 318/558; 318/671; 307/326
[58] Field of Search ................. 318/568.16, 652, 671, 318/558, 565, 566; 128/846, 897, 908; 269/23, 289 R, 290-329; 307/326, 112, 113, 115, 116, 119; 361/170, 179, 181, 189, 190

[56] References Cited

U.S. PATENT DOCUMENTS

| 4,105,899 | 8/1978 | Velosa | 307/115 |
| 4,237,421 | 12/1980 | Waldron | 328/5 |
| 4,303,829 | 12/1981 | Wagner | 250/445 T |
| 4,951,786 | 8/1990 | Haraguchi | 187/1 R |
| 5,034,621 | 7/1991 | Groves et al. | 307/117 |

FOREIGN PATENT DOCUMENTS

| 2149240 | 4/1973 | Fed. Rep. of Germany |
| 2529475 | 1/1977 | Fed. Rep. of Germany |
| 2148760 | 7/1981 | Fed. Rep. of Germany |
| 3604955 | 8/1987 | Fed. Rep. of Germany |
| 3811380 | 1/1989 | Fed. Rep. of Germany |

Primary Examiner—Bentsu Ro
Attorney, Agent, or Firm—Hill, Van Santen, Steadman & Simpson

[57] ABSTRACT

A medical apparatus has an apparatus part which is motor-adjustable relative to a surface in a direction of at least one degree of freedom. A sensing card means comprising a plurality of sensing cards forms a matrix-like grid which is attachable to the surface in a range of adjustment of the apparatus part. The sensing cards each output a signal given the presence of a subject in the region of the respective sensing card. The signals output by these sensing cards are evaluated in dependence upon the desired adjustment direction in such a way that only the sensing card or cards of the matrix-like grid lying in the desired adjustment direction is or are taken into consideration. An adjustment of the apparatus part in the desired adjustment direction is suppressed when at least one sensing card taken into consideration outputs a signal indicating the presence of a subject.

9 Claims, 4 Drawing Sheets

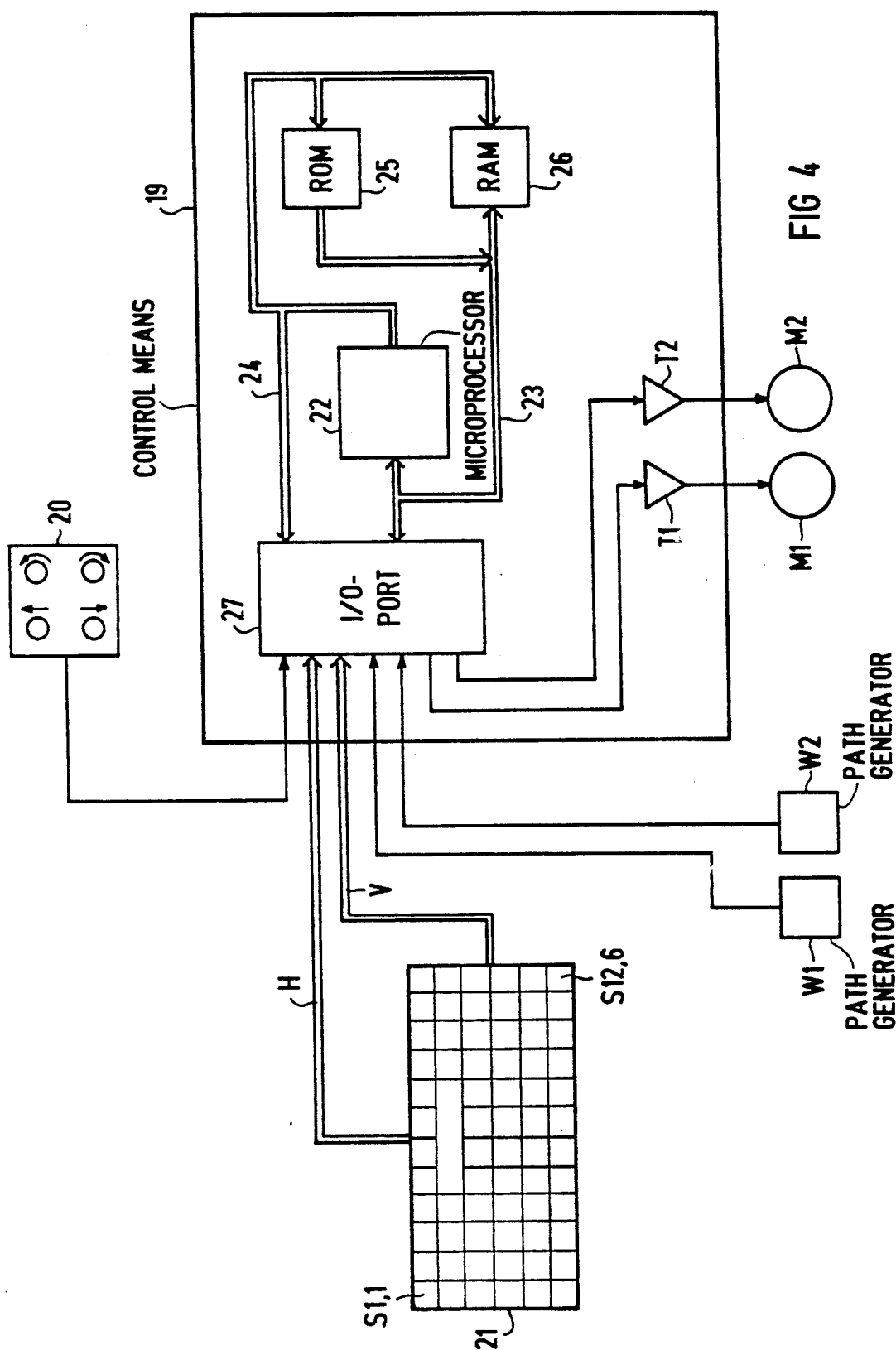

MEDICAL APPARATUS HAVING AN APPARATUS PART WHICH IS MOTOR-ADJUSTABLE RELATIVE TO A SURFACE IN A DIRECTION OF AT LEAST ONE DEGREE OF FREEDOM

BACKGROUND OF THE INVENTION

The invention is directed to a medical apparatus having an apparatus part which is motor-adjustable relative to a surface in a direction of at least one degree of freedom. A control means is provided for adjusting the apparatus part. A sensing card means is attachable to the surface and outputs a signal given presence of a subject in a region of the sensing card means. This signal is supplied to a control means which suppresses an adjustment of the apparatus part, given the presence of the signal. The term "subject" is intended to cover both life forms as well as articles.

In medical apparatus having an apparatus part which is adjustable relative to a surface—such as diagnosis or therapy apparatus—there is always a risk of injury for the operating personnel and also potentially for the patient since their bodies, particularly their extremities, can be clamped between the adjustable apparatus part and the surface. There is also the risk of damage to the apparatus when a foreign body is situated between the adjustable apparatus part and the surface. Efforts have thus been undertaken to suppress the risk of injury for the operating personnel and for the patient, as well as to suppress the risk of damage to the apparatus. For example, markings as well as sensing panels or cards to be applied to the respective surfaces are known as solutions to reduce these risks (DE-AS 21 49 240, German Patent 21 48 760 and German Published Application 38 11 380, all incorporated herein by reference). Markings, however, are only optical indications that are not always observed. Sensing cards can only represent a compromise in terms of their size and arrangement on the surface. First, there is the possibility of covering the entire endangered region with the consequence that, for example, disturbing interruptions or, respectively, inhibitions of the apparatus movement occur as a consequence of a person stepping on the sensing panel or card means without a risk to the person being actually established. If this disadvantage is to be avoided, on the other hand there is the possibility of making the sensing panel or card smaller, with the consequence that the entire endangered area is no longer protected to an adequate degree.

An x-ray apparatus disclosed in DE-AS 21 49 240 represents an improvement in that a plurality of sensing panels or card means allocated to individual risk zones is provided, these only taking affect when the adjustable apparatus part has approached the corresponding risk zone beyond a defined degree (the position of the adjustable apparatus part is monitored with the assistance of position-dependent switches) and the respectively desired apparatus motion would effect a further approach of the adjustable apparatus part to the risk zone. Here, too, however, there is the risk of unnecessary interruptions or inhibitions of apparatus movements, which can again only be avoided by making the circuit card allocated to the respective risk zone smaller, with the consequence that an adequate protection is then no longer guaranteed under all circumstances.

SUMMARY OF THE INVENTION

An object of the invention is to design an apparatus of the type initially cited such that a safeguarding of the entire danger region is guaranteed in a simple, dependable way which is easily adaptable to changing requirements, and wherein interruptions or inhibitions of the movement of the apparatus part are nonetheless reliably avoided when an immediate risk is not present.

This object is inventively achieved by a medical apparatus having an apparatus part which is motor-adjustable relative to a surface in the direction of at least one degree of freedom. A control means is provided for adjusting the apparatus part. A sensing panel or card means is provided having a plurality of sensing cards forming a matrix-like grid and which is attachable to a surface in a range of adjustment of the apparatus part. The sensing cards respectively output a signal, given the presence of a subject in the region of the respective sensing card. These signals of the individual sensing cards or panels of the matrix-like grid are supplied to the control means. The control means evaluates the signals output by the sensing cards in dependence upon a desired adjustment direction in such fashion that it only takes the sensing card or cards of the matrix-like grid which are immediately proximate to the apparatus part in the direction of the desired adjustment direction into consideration, and suppresses an adjustment of the apparatus part in the desired adjustment direction when at least one sensing card taken into consideration outputs a signal indicating the presence of a subject.

Since in the invention the sensing cards or panels of the sensing card or panel means form a matrix-like grid, and only the sensing cards critical for the respective situation are taken into consideration, it is assured that unnecessary interruptions or inhibitions of the movement of the adjustable apparatus part are reliably avoided. This is true regardless of whether the entire region at risk due to the adjustable apparatus part is protected with the grid or only an individual, specific risk zone within a larger region at risk is protected with the sensing card means. It is thus critical that, as a consequence of the matrix-like design of the sensing card means, the motion of the apparatus part is not already suppressed, i.e. interrupted or inhibited, when a subject is situated at an arbitrary location within a potential risk region secured by the sensing card means. Rather, the motion is only suppressed when this subject assumes a position within the protected risk region such that it is situated in an acutely jeopardized region. A faultless protection is nonetheless guaranteed since all sensing cards in whose region an acute risk could occur are taken into consideration by the control means, whereby respectively different sensing cards are taken into consideration by the control means, dependent on the respective position of the adjustable apparatus part. By contrast to the prior art, the solution of the invention thus does not represent a compromise of the type initially cited, but permits a complete protection of the risk region or of individual risk zones, without the risk of unnecessary disturbances of the existing movement of the apparatus part. The subdivision of the matrix-like grid of the sensing cards forming the sensing card means is to be selected in accordance with a respective application such that unnecessary impediments to the movement of the apparatus part are avoided, or are limited to an acceptable minimum. An even finer subdivision of the grid which goes even further would result in the expense required for the sensing card means rising due to the greater number of sensing cards, without this being counterbalanced by a noteworthy advantage. A simple and dependable structure results as a consequence of formatting the sensing card means as a matrix-like grid of, for example, capacitative or inductive sensing cards. Changing requirements that could result, for example, in additional or different movements of the movable apparatus part are introduced for the implementation of new therapies or examinations which can be easily taken into consideration, since the control is adapted to the new requirements. This is particularly easy when the control is programmable and, as necessary, additional sensing cards are added to the grid. In the present case, the term "immediately proximate" should be understood such that the distance of the adjustable apparatus part from the surface carrying the sensing card means falls below a defined minimum distance measured at a right angle relative to the surface. Dependent on the respective, special conditions, for example, the minimum distance can lie on the order of magnitude of a few millimeters up to approximately 0.5 m. Preferably, the control means has means allocated to it for identifying the momentary position of the apparatus part being supplied to the control means which evaluates the signals output by the sensing cards while consulting the output signals of the means for identifying the momentary position of the apparatus part. The means for identifying the momentary position of the apparatus part, moreover, can be a matter of traditional path generators. When the apparatus part is adjusted by stepping motors, the means for identifying the momentary position of the apparatus part can also be formed by the drive circuit for the stepping motors whose output signals then identify the momentary position of the apparatus part. It is critical in both instances that, differing from the case of position-dependent switches, a practically continuous monitoring of the position of the apparatus part is possible which has a beneficial influence on avoiding unnecessary impediments to the movement of the apparatus part.

A simple, dependable structure of the control means that is easily adaptable to changing requirements is guaranteed when, in an especially preferred and advantageous modification of the invention, it is provided that the control means comprises a memory in which the sensing card or cards to be taken into consideration is or are stored for a plurality of positions of the apparatus part, and for the respectively possible adjustment direction or directions of the apparatus part proceeding from these positions. In the case of such a control means, thus the sensing card or cards to be taken into consideration are thus called in from the memory, dependent on the output signals of the means for identifying the momentary position of the apparatus part when an adjustment of the apparatus part is to occur. Thus, the memory can be easily reprogrammed for adaptation to changing requirements. Although a control means having a memory as set forth is particularly advantageous given sensing card means having sensing cards forming a matrix-like grid, it can also be advantageously utilized in conjunction with sensing card means that are not designed as a matrix-like grid.

The matrix-like grid can contain circuit cards which act in a pressure-sensitive and/or capacitive manner. If capacitive, they then offer the advantage that they can supply a signal not only when a subject is situated on the sensing card, but also when a subject is in the region of the sensing card without touching it. For consideration as pressure-sensitive sensing cards are, for example, electromechanical sensing cards as disclosed in German Patent 21 48 760. The sensing cards disclosed by German Published Application 38 11 380 can be employed as capacitively acting sensing cards.

It will usually be provided that the sensing card means can be applied to the floor or to a wall of the room in which the medical apparatus is erected. However, cases are also conceivable wherein an application of the sensing card means occurs at a surface of the apparatus itself relative to which the apparatus part is adjustable.

BRIEF DESCRIPTION OF THE DRAWINGS

FIG. 4 is a block circuit diagram of the control system of the apparatus of FIGS. 1 through 3.

DESCRIPTION OF THE PREFERRED EMBODIMENTS

Figure 1:
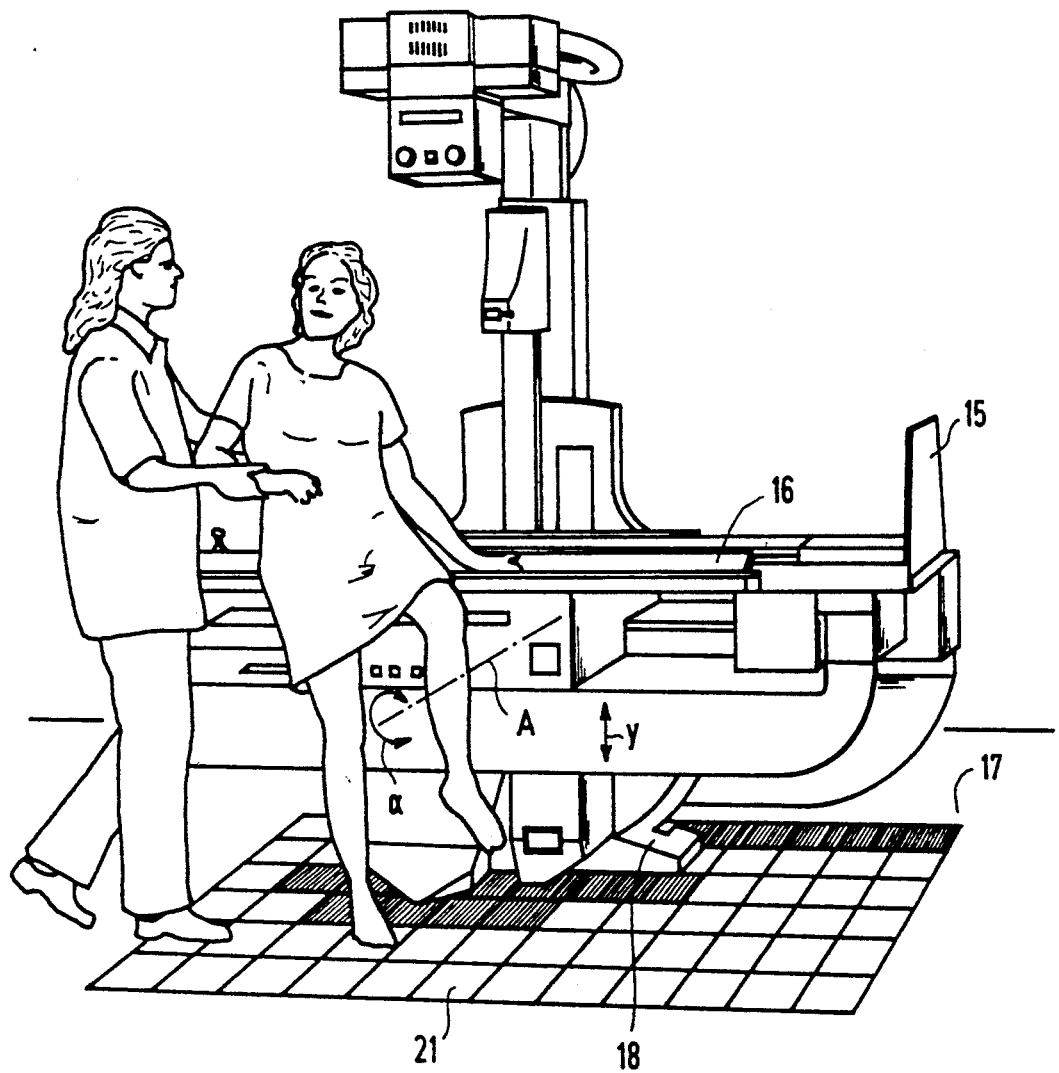
FIGS. 1 through 3 show different operating conditions of an apparatus of the invention.
Figure 2:
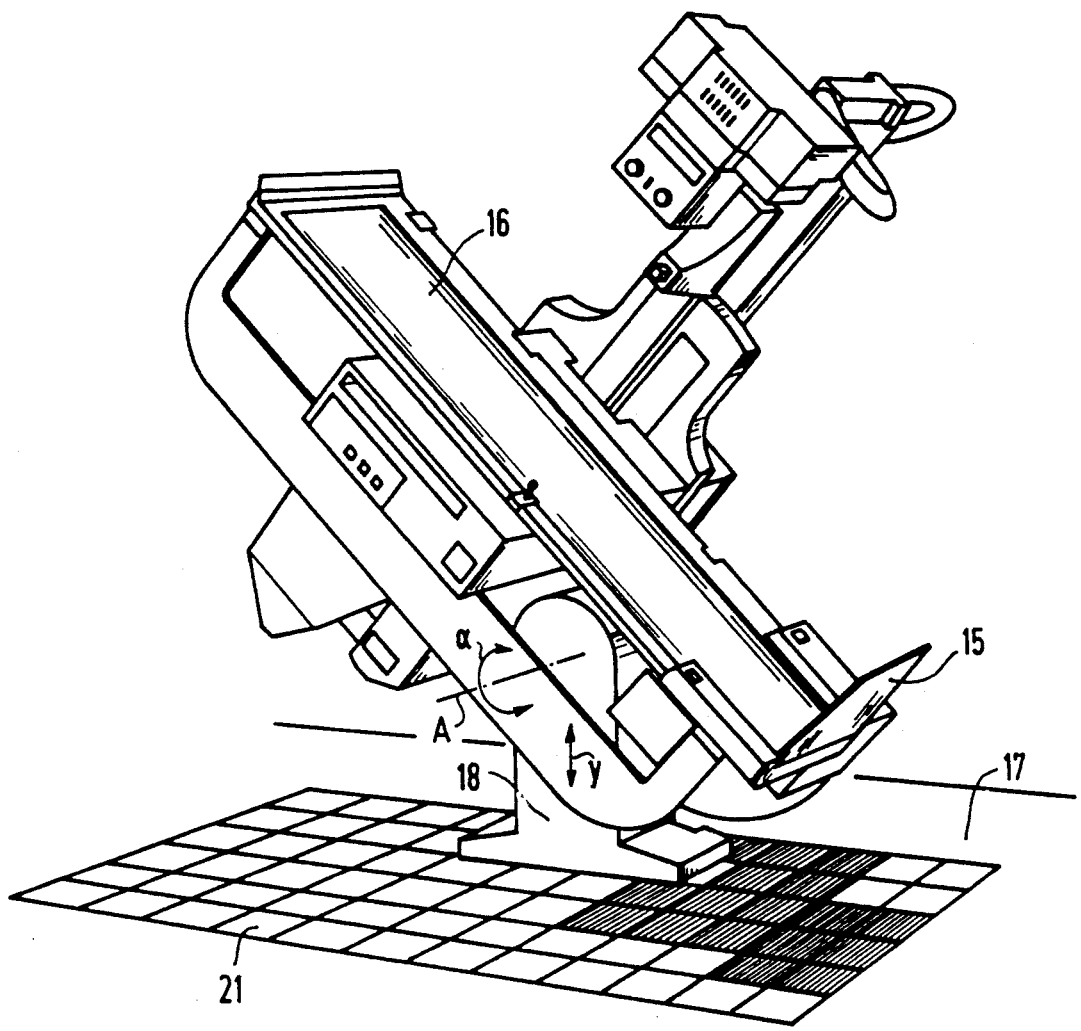
Figure 3:
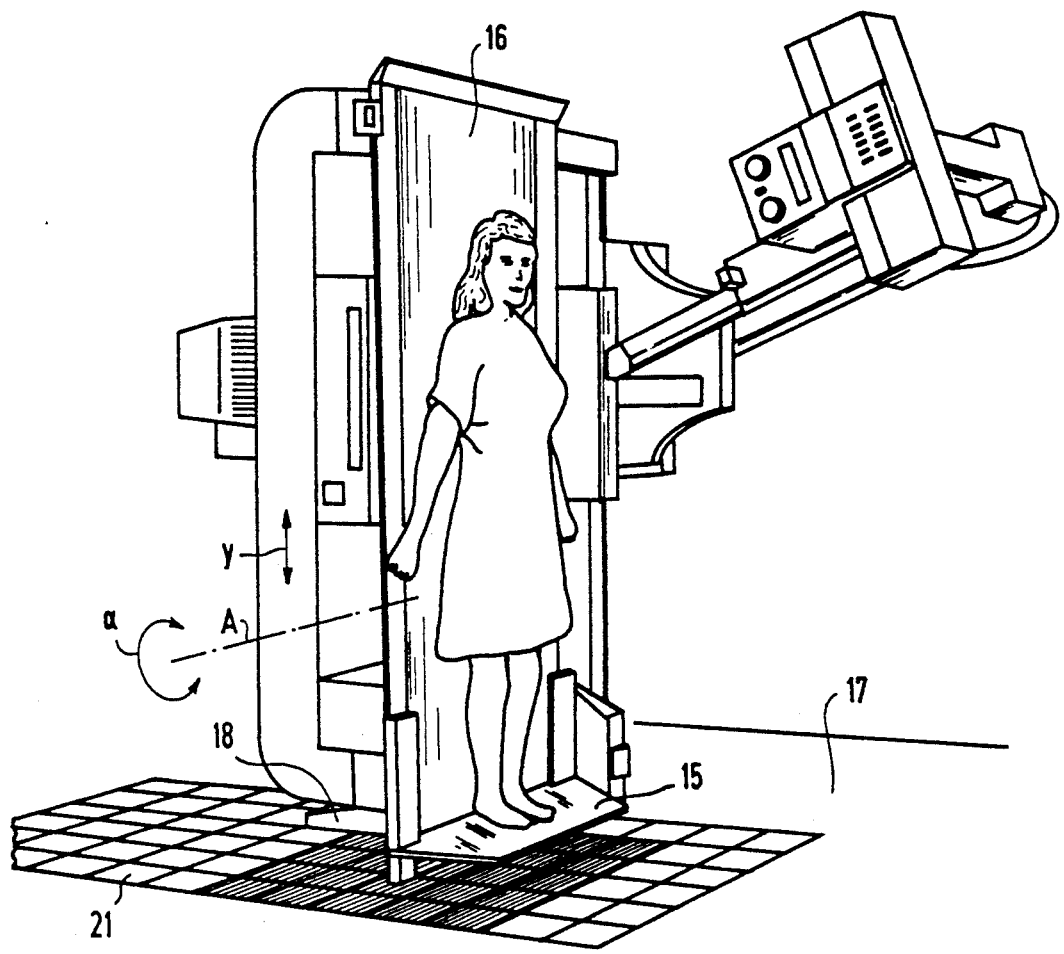

FIGS. 1 through 3 show a known x-ray examination apparatus whose function is of interest here only insofar as the patient support table 16 thereof provided with a foot rest 15 is motor-adjustably attached to a pedestal 18 secured to the floor 17 of the examination room. In detail, the patient support table 16 is attached to the pedestal 18 to be height-adjustable with an electric motor M1 (FIG. 4) in the direction of the straight-line double arrow y in a known way which is not shown. In a way that is likewise known and not shown, the patient support table 16 can be pivoted with the assistance of the electric motor M2 (FIG. 4) in the direction of the curved double arrow "alpha" around an axis A that proceeds horizontally and transversely relative to the longitudinal axis of the patient support table 16.

As FIG. 4 schematically shows, the control of the movement of the patient support table 16 occurs with a control means 19 which drives the electric motors M1 and M2 as required by the actuation of a keyboard 20 connected to the control means 19. The keyboard 20 has pairs of keys for every adjustment direction of the patient support table 16 as are identified by appropriate arrow symbols. The keys thereof serve the purpose of effecting the respective movement in the one or in the other direction. In addition to the keyboard 20 and the electric motors M1 and M2, two path generators W1, W2 which can, for example, be inductive path generators, are connected to the control means 19. These supply electrical signals corresponding to the position of the patient support table 16 relative to the pedestal 18, and thus relative to the floor 17. Thus, the path generator W1 is responsible for the direction y and the path generator W2 is responsible for the direction "alpha".

A sensing card or panel means which, as may be seen from FIGS. 1 through 3, is attached to the floor 17 of the examination room in the region of the x-ray examination apparatus, is also connected to the control means 19. The sensing card or panel means comprises a plurality of sensing cards or panels S1,1 through S12,6 arranged in the form of a matrix-like grid 21 having six rows and twelve columns. The first numeral references the column and the second numeral references the row of the matrix-like grid 21 in which a sensing card is situated. The positions S5,2 through S8,2 are not occupied since the pedestal 18 is situated here. The sensing cards S1,1 through S12,6—which preferably involve capacitively acting sensing cards or panels that can be designed in conformity with German Published Application 38 11 380 —then respectively output a signal when a subject is situated in their region. The sensing cards or panels S1,1 through S12,6, however, can also be designed as pressure-sensitive sensing cards or panels conforming to German Patent 21 48 760. The matrix-like grid 21 of the sensing card means is connected to the control means 19 via two line lanes H and V combined in bus-like fashion such that each of the sensing cards S1,1 through S12,6 which supply a signal indicating the presence of a subject can be unambiguously identified by the control means 19. The sensing card means serves the purpose of suppressing movements of the patient support table which could lead to injuries to a person or to damage of the x-ray examination apparatus.

In a known way, the control means 19 contains a microprocessor 22 which is connected via a data bus 23 and an address bus 24 to a read-only memory (ROM) 25, to a random access memory (RAM) 26, and to an input/output wiring (I/0 port) 27. The keyboard 20, the sensing card means, the path generators W1 and W2, and the electric motors M1 through M2 are connected to the I/0 port 27. The electric motors M1 through M2 have corresponding driver stages T1 and T2 allocated to them. In addition to a control program which guarantees the functioning of the control means 19 set forth below, certain of the sensing card or cards of the matrix-like grid 21 is or are stored in the ROM 25. These certain cards are those which is or are to be taken into consideration for a plurality of positions of the patient support table 16 relative to the pedestal 18 and for the adjustment direction of the patient support table 16 that are possible, proceeding from these positions. The data arising during operation of the apparatus are intermediately stored in the RAM 26.

When one of the keys of the keyboard 20 is actuated, the microprocessor 22 receives data via the I/0 port 27 and makes it possible for the microprocessor to identify the actuated key of the keyboard 20. Thereafter, the microprocessor 22 accepts data corresponding to the output signals of the path generators W1 and W2 via the I/0 port 27. With this data the microprocessor calculates the momentary position of the patient support table 16 relative to the pedestal 18. Taking this position and the desired adjustment direction, i.e. the actuated key of the keyboard 20 into consideration, the microprocessor 22 calls data in from the ROM 25 which indicates which of the sensing cards or panels S1,1 through S12,6 of the matrix-like grid 21 of the sensing card means is or are to be taken into consideration for the desired adjustment direction of the patient support table 16 proceeding from the momentary position of the patient support table 16. This is for the purpose of being able to suppress a risk, whether it is the risk to a person as a result of the moving patient support table 16, or a risk to the patient support table 16 itself such as by striking a foreign body or the floor 17. After it has read the corresponding data from the ROM 25, the microprocessor 22 queries the sensing cards of the matrix-like grid 21 of the sensing card means to be taken into consideration via the I/0 port 27. If no sensing card to be taken into consideration supplies a signal indicating the presence of a subject, the microprocessor 22 drives the motors M1 or M2 which determine the desired movement of the patient support table 16 in the corresponding direction. As a result thereof, the position of the patient support table 16 changes relative to the pedestal 18, this also leading to a change in the output signals of the path generators W1, W2. The changing output signals of the path generators are monitored by the microprocessor 22 for the entire duration during which a key of the keyboard 20 is actuated. During this duration, the microprocessor 22 continuously calls the circuit card or cards of the matrix-like grid 21 to be taken into consideration in accordance with the changing position of the patient support table 16. In accordance with the selected moving direction from the ROM 25, the microprocessor queries the sensing card or cards respectively to be taken into consideration in the way set forth above. It thus becomes clear that, together with the changing position of the patient support table 16 during the course of the movement of the patient support table 16, the control means 19 may gradually consider different sensing cards than were considered at the beginning of the movement.

When, during the motion of the patient support table 16, no sensing card to be taken into consideration supplies a signal indicating the presence of a subject, the desired motion is continued as long as the corresponding key of the keyboard 20 is depressed, unless known limit switches (not shown) respond. When, following the pressing of a key of the keyboard 20, the microprocessor 22 determines that a sensing card of the matrix-like grid 21 of the sensing card means immediately proximate to the patient support table 16 in the desired adjustment direction, outputs a signal indicating the presence of a subject, the desired motion is not initiated until the subject has moved away or has been removed. When a sensing card to be taken into consideration supplies a signal indicating the presence of a subject while a movement of the patient support table 16 is already being executed, the microprocessor 22 interrupts the movement since it suppresses the further drive of the corresponding motor M1 or M2.

As can be easily imagined with reference to FIGS. 1 through 3 which illustrate a lifting of the initially horizontal patient support table 16 into a vertical position, a changing pattern of sensing cards is to be taken into consideration, as illustrated and emphasized by hatching in the case of FIGS. 1 through 3. The pattern thus "migrates" across the matrix-like grid 21 of the sensing card means during the movement. Accordingly, those sensing cards that are immediately proximate to the patient support table 16 are respective sensing cards to be taken into consideration. What is meant by immediately proximate are those parts or regions of the patient support table, the distance of which from the floor 17 measured at a right angle relative to the floor 17, falls below a minimum distance which identifies an acute risk.

It becomes clear that the risk of inherently unnecessary disturbances in the motion of the patient support table is reduced in practical fashion since the adjustment of the patient support table 16 is not interrupted when a subject is situated on the matrix-like grid 21 of the circuit card means in the desired adjustment direction, but at a greater distance from the patient support table 16. It is only interrupted when a subject is situated in an acute risk situation in the desired adjustment direction in the immediate proximity of the patient support table 16.

Although various minor changes and modifications might be proposed by those skilled in the art, it will be understood that I wish to include within the claims of the patent warranted hereon all such changes and modifications as reasonably come within my contribution to the art.

I claim as my invention:

1. A medical apparatus, comprising:
an apparatus part and means for motor-adjustable positioning of the apparatus part relative to a surface in a direction of at least one degree of freedom;
control means for controlling the adjustment of the apparatus part, said control means having a sensing card means connected thereto comprising a plurality of sensing cards forming a matrix-like grid and attached to the surface in a range of adjustment of the apparatus part, said sensing card means outputting a respective signal associated with at least one of the sensing cards given presence of an object in a region of the respective ones of said sensing cards; and
said control means evaluating said respective signal outputted by the sensing cards in dependence on a desired adjustment direction of the apparatus part such that it only takes into consideration the signals of those sensing cards of the matrix-like grid which are immediately proximate to the apparatus part in said desired adjustment direction, and suppresses an adjustment of the apparatus part in the desired adjustment direction when at least one sensing card taken into consideration outputs a signal indicating the presence of the object.

2. A medical apparatus according to claim 1 further comprises a path generator means, and wherein said control means is connected to said path generator means for identifying a momentary position of said apparatus part, and evaluates the signals outputted by the sensing cards after considering the momentary position of the apparatus part.

3. A medical apparatus according to claim 1 wherein said control means has a memory for storing the status of the sensing cards and for adjusting the direction of the apparatus part based on its position.

4. A medical apparatus according to claim 1 wherein the sensing card means contains pressure-sensitive sensor cards.

5. A medical apparatus according to claim 1 wherein the sensing card means contains capacitively acting sensor cards.

6. A medical apparatus according to claim 1 wherein the sensing card means is attached to the floor of a room in which the medical apparatus is erected.

7. A medical apparatus according to claim 1 wherein the sensing card means is attached to the wall of a room in which the medical apparatus is erected.

8. A medical system, comprising:
a patient table and means for motor-adjustable positioning of the patient table relative to a surface in a direction of at least one degree of freedom;
control means for controlling the adjustment of the patient table, said control means being connected to a sensing card means comprising a plurality of sensing cards forming a matrix-like grid and attached to the surface in an adjustment region of the patient table, said sensing card means outputting a respective signal associated with each sensing card which detects the presence of an object in a region thereof; and
said control means evaluating said respective signals outputted by the sensing card means based on a desired adjustment direction of the patient table such that it only takes into consideration the respective signals of those sensing cards of the matrix-like grid which are predetermined to be a hazard for said desired adjustment direction if the object is in the region thereof and suppresses an adjustment of the patient table in the desired adjustment direction when at least one sensing card taken into consideration inputs a signal indicating the presence of the object.

9. A medical system according to claim 8 wherein said control means includes memory means for storing the status of a different pattern of cards in said matrix-like grid determined to be in a hazard zone for each of a plurality of different positions of the patient table.

* * * * *

UNITED STATES PATENT AND TRADEMARK OFFICE
CERTIFICATE OF CORRECTION

PATENT NO. : 5,166,588

DATED : November 24, 1992

INVENTOR(S) : Klaus Goldhorn

It is certified that error appears in the above-identified patent and that said Letters Patent is hereby corrected as shown below:

On the Title page, item [21], Application No., change "600,423" to -- 660,423--.

Signed and Sealed this

Thirtieth Day of November, 1993

Attest:

BRUCE LEHMAN

*Attesting Officer*  *Commissioner of Patents and Trademarks*